United States Patent
Mikulsky

[19]

[11] Patent Number: 6,146,595
[45] Date of Patent: Nov. 14, 2000

[54] CLOSED EVAPORATOR SYSTEM FOR PREPARING SAMPLES FOR ANALYSIS

[75] Inventor: John J. Mikulsky, San Carlos, Calif.

[73] Assignee: Balazs Analytical Laboratory, Sunnyvale, Calif.

[21] Appl. No.: 09/021,684

[22] Filed: Feb. 10, 1998

[51] Int. Cl.[7] .................................. B01L 7/00; B01D 1/14
[52] U.S. Cl. .............................. 422/101; 422/63; 422/81; 422/100; 422/103; 422/104; 436/175; 436/177; 436/180
[58] Field of Search .................... 422/63, 81, 100, 422/101, 103, 104; 436/175, 177, 180

[56] References Cited

U.S. PATENT DOCUMENTS

| 4,604,363 | 8/1986 | Newhouse et al. | 436/177 |
|---|---|---|---|
| 4,707,452 | 11/1987 | Friswell | 436/177 |
| 4,708,886 | 11/1987 | Nelson | 422/72 |
| 5,100,623 | 3/1992 | Friswell | 422/68.1 |
| 5,217,572 | 6/1993 | Guy et al. | 159/6.1 |
| 5,514,336 | 5/1996 | Fox | 422/64 |
| 5,621,847 | 4/1997 | Tillotson et al. | 392/391 |
| 5,897,838 | 4/1999 | Kempe | 422/101 |

*Primary Examiner*—Long V. Le
*Assistant Examiner*—Kathryn Bex
*Attorney, Agent, or Firm*—Edward M. Suden

[57] ABSTRACT

A closed positive pressure evaporation system for evaporating samples in preparation for analysis comprising a plurality of sample vials where each sample vial has associated therewith an inlet and an outlet. A chamber is provided having a heat source and a holder for positioning and holding the sample vials with reference to the heat source. A distribution manifold is connected via tubing to the inlet of each sample vial for distributing purified inert gas, such as Nitrogen, to each sample vial held by the holder in the chamber. A collection manifold is connected via tubing to the outlet means of each sample vial for collecting purified inert gas, such as Nitrogen, and gases from each sample vial connected to the distribution manifold. The chamber, distribution manifold and collection manifold coacting to expose a sample in each sample vial to only purified inert gas, such as Nitrogen, during the evaporation of the sample.

8 Claims, 3 Drawing Sheets

CLOSED EVAPORATOR SYSTEM FOR PREPARING SAMPLES FOR ANALYSIS

BACKGROUND OF THE INVENTION

1. Field of the Invention

The present invention generally relates to an evaporator system. More particularly, the present invention relates to a closed evaporator system for preparing samples for chemical analysis.

2. Description of the Related Art

In many industries, including the semiconductor fabrication industry, knowledge of the level of contaminates in a chemical solution and of the air in is the processing areas is extremely important. Analytical laboratories receive sample vials, or the like, containing samples of chemical solutions and of airborne contaminates dissolved in water or other solutions. In order to assay the samples for the type and quantity of contaminates, the samples are evaporated such that the relative concentration of the contaminates is increased ideally resulting in only solid matter remaining for the sample. It is usual for an analytical laboratory to ascertain that the laboratory's handling of a sample has not added further contaminates and the analytical procedures are accurate. To this end, the laboratory will include a known blank sample (no contaminates or a known type and amount of contaminates) and process the blank sample along with the actual samples. When the analysis is completed for the blank sample, the laboratory can ascertain the type and quantity of any contaminates added to the sample due to processing within the laboratory. The laboratory will also process a control sample having a known quantity and type of solids to ascertain the accuracy of the analytical procedure. It is desirable to expose the blank and the control samples to the same conditions as possible as experienced by the samples to be analyzed.

The sensitivity of an analytical procedure is increased as the level of laboratory's contamination of the sample is decreased. For example, if the laboratory added contaminate X in the quantity of 500 ppm (parts per million) plus or minus 50 ppm, an analytical test for contaminate X can have no greater sensitivity than 50 ppm.

A present open evaporation system for evaporating samples in shown in FIG. 1. A hot plate 11 having heat control 12 is used for heating the sample to cause evaporation of the sample. The sample is placed in a high purity fluoropolymer, such as TEFLON™, bowl 14 which sits in a petri dish 13 which in turn sits upon hot plate 11. A high purity fluoropolymer gas input cover 15, commonly referred to as a thier, covers bowl 14 and receives a purified inert gas such as Nitrogen from an unregulated gas source through inlet 16. Overhead heat lamp 17 is provided to avoid condensation from occurring onto the thier 15. The entire system is located under a venting hood 18. The evaporation of the sample takes place in a purified inert gas, such as Nitrogen, atmosphere. The vapors from the evaporation process, as indicated by the arrows, flow from the sample into the chamber formed by the thier 15 and petri dish 13, out of that chamber from around the edge of the thier 15 contacting petri dish 13 and then up into the venting hood 18. Such an open evaporation system has an average evaporation rate of 15 ml/hr and a sensitivity of approximately 10 ppm. The actual evaporation rate is determined by the density of the chemical being evaporated.

An open evaporator system for processing a plurality of samples is discussed in U.S. Pat. No. 5,514,336 entitled "Automated Evaporator For Chemical Analysis". Here the samples are in open vials which are partly submerged in heated water to cause evaporation of the samples. A purified inert gas, such as Nitrogen, source is provided through a regulator to a manifold which distributes purified inert gas, such as Nitrogen, to each of the samples. The Purified inert gas, such as Nitrogen, helps to remove the solvent vapors and limits oxidizing of the samples by displacing oxygen from the air.

A closed negative pressure evaporator system for processing a single sample is discussed in U.S. Pat. No. 5,612,847 entitled "Dynamic Vacuum Evaporation System". Here the sample is in a closed vessel which is covered partially by a cover on five sides and exposed to a heater on the six side to cause evaporation of the samples. A purified inert gas, Argon, source is provided under negative pressure to the sample in the vessel while the sample is being evaporated. The purified inert gas, picks up the volatiles from the sample which is evacuated from the vessel by the vacuum pump. There is, however, some risk of explosion if the system is not operated properly.

SUMMARY OF THE INVENTION

It is an object of the present invention to provide a closed evaporation system that permits processing of a plurality of samples along with a blank sample and a control sample.

It is another object of the present invention to provide a closed evaporation system that has sensitivity in the range of 1 ppb (part per billion).

Briefly the invention is a closed positive pressure evaporation system for evaporating simultaneously a plurality of samples. Purified inert gas, such as Nitrogen, flows from a source through a regulator to a multiple port distribution manifold where each port may be individually open or closed. A chamber encloses on all sides a controllable heat source and a holder for holding the plurality of samples in a desired relationship to the heat source. Tubing connected to each port of the distribution manifold passes into the closed chamber. The samples are contained in sample vials where each vial has an inlet and an outlet and a length of tubing connecting the inlet to the outlet, thereby sealing the sample vial. A collection manifold is provided, having a plurality of ports where each port may be individually open or closed. Tubing connected to each port of the distribution manifold passes into the closed chamber. When a sample vial is placed in the holder in the chamber, the tubing is removed from the outlet of the sample vial and connected to the tubing extending from one of the ports of the distribution manifold and tubing from one of the ports of the collection manifold is connected to the outlet sample vial. The outlet of the collection manifold is connected via tubing to a scrubber which, in turn, is connected to a waste flask for collecting waste fluids and venting fumes into a venting hood. After the samples have been evaporated, the distribution and collection manifold tubing is removed from the sample holder and the sample holder's tubing is again attached between the inlet and the outlet of the sample holder.

An advantage of the invention is that during the period of time that a sample is being evaporated the sample is only exposed to a purified inert gas, such as Nitrogen, atmosphere.

Another advantage of the invention is that the temperature of the samples can be raised to increase the evaporation rate while not bringing the samples to a boiling point thereby reducing processing time.

Another advantage of the invention is that the sample is not exposed to the environment of the laboratory thereby increasing the sensitivity of the analytical process.

Another advantage of the invention is that the evaporation system is under positive pressure removing any danger of an explosion occurring during normal processing.

BRIEF DESCRIPTION OF THE DRAWINGS

The invention will be described with respect to the particular embodiments thereof and references will be made to the drawings, in which.

DETAILED DESCRIPTION OF THE INVENTION

Figure 2:
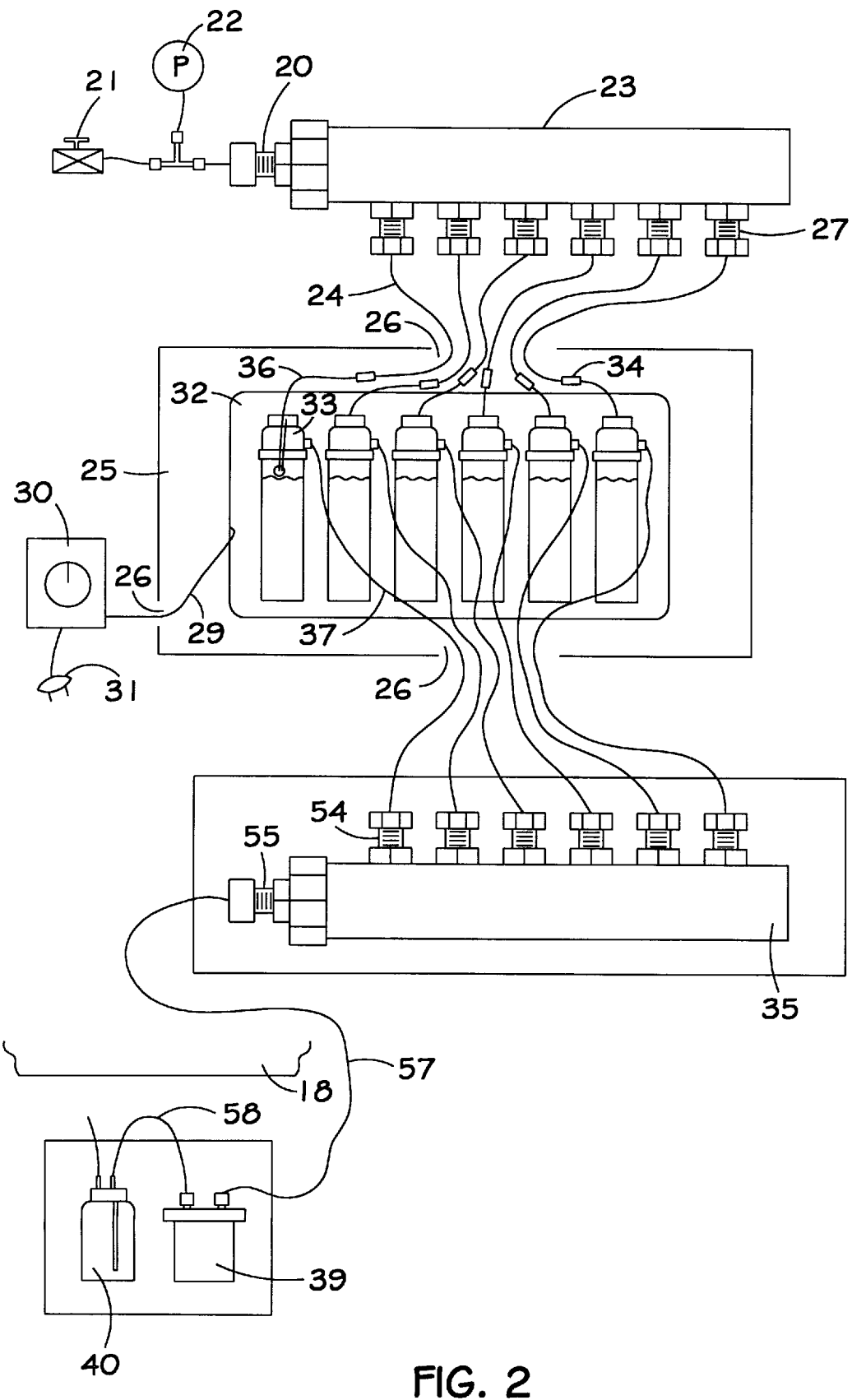
FIG. 2 is a diagram of the structure of the closed positive pressure evaporation system of the invention.

Referring to FIG. 2, the closed positive pressure evaporator system is shown to be composed of a distribution manifold 23 having an input port 25 and six exit ports 27 where each exit port 27 can be individually open or closed. A source of purified inert gas, such as Nitrogen, (not shown) is supplied to valve 21, which is connected to pressure gauge 22, for controlling the flow rate of purified inert gas, such as Nitrogen, to the closed positive pressure evaporation system. The valve 21 contains a 0.2 $\mu$ PTFE particle filter, the output of which is connected to the input port 20 of distribution manifold 23. All tubing herein referred to is TEFLON™ tubing. Each exit port 27 of the distribution manifold 23 has tubing 24 attached thereto which terminates in a connector 34B, one half of connector 34, and the tubing 24 extends into chamber 25 through inlet 26 in the distribution chamber's side wall.

Figure 3:
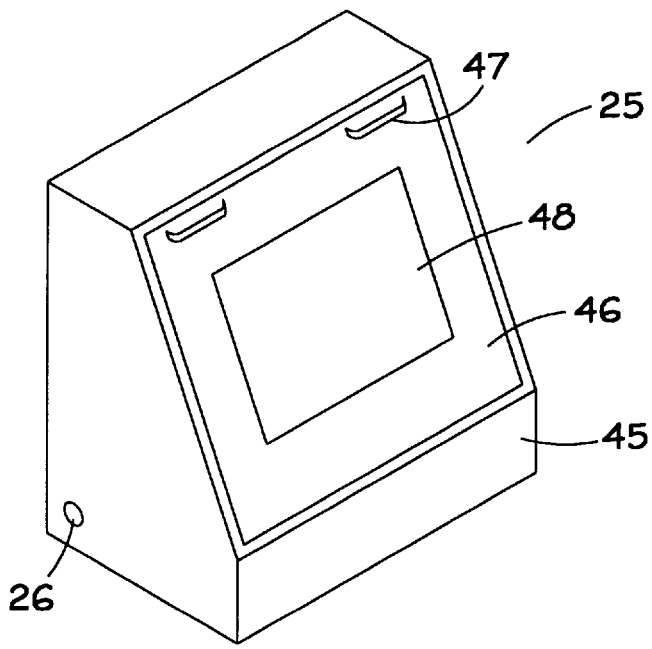
FIG. 3 is an isometric view of the outside of the chamber of the invention.

Referring to FIG. 3, chamber 25 is shown to have a housing 45 and a removable front plate 46 which is slid into slots (not shown) in the front on housing 46. Front plate 46 includes handles 47 to aid in the removal of front plate 46 from housing 45 and an optional window 48 to allow viewing into the chamber 25.

Figure 5:
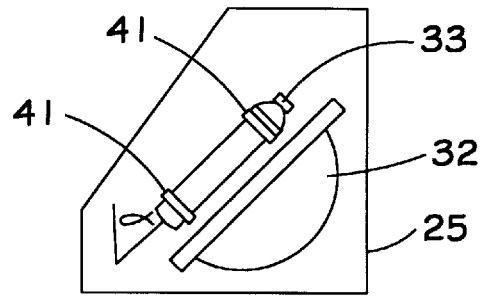
FIG. 5 is a diagram showing the relative positions of the samples with relationship to the heat source.

Referring to FIG. 5, an infrared heat source 32 is mounted at an angle α in chamber 25 and is connected via wire 29 to a variable autotransformer 30 (see FIG. 2) which in turn is connected via plug 31 to a 220 AC voltage source. An acceptable heat source is a 1500 watt, 240 volt infrared lamp from Sylvania bearing the product number SLY1500T3QCL240. The selected lamp should be rectangular in shape and have internal reflectors such that the energy radiated from the rectangular face of the lamp is approximately evenly distributed. Two sample holders 41 are mounted within evaporation unit 25 perpendicular to the face of heat source 32 such that sample vials 33 when in sample holders 41 will be parallel to the face of the heat source 32. Heat source 32 and sample vials 33 are at an angle such that a larger portion of the sample within sample vial 33 is exposed to the ultraviolet radiation from the heat source 32. The angle α range should be from 25 to 45 degrees.

Figure 6:
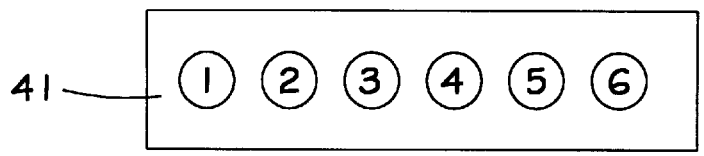
FIG. 6 is a diagram of a six position holder used in the chamber of the closed positive pressure evaporation system of the invention.

Referring to FIG. 6, the sample holder 41 is made from TEFLON™ coated aluminum and has six holes for receiving six sample vials 33. The holes should be located as close as possible such that all six holes are within, where possible, the parameters of the face of the heat source 32 such that all six sample vials are exposed directly to the ultraviolet energy radiating from the heat source.

Typically, known heat sources 32 do not provide uniform heating across the face of the heat source 32 and the size of the sample vials may not allow the entire portion of sample vials 1 and 6 to be within the parameters of the face of the heat source 32. To assist in providing a uniform temperature profile across all six sample vials, the interior walls of chamber 25 are coated with white TEFLON™ so as to reflect the radiant energy from the heat source 32 and no window is provided in front plate 46 of chamber 25.

Figure 4:
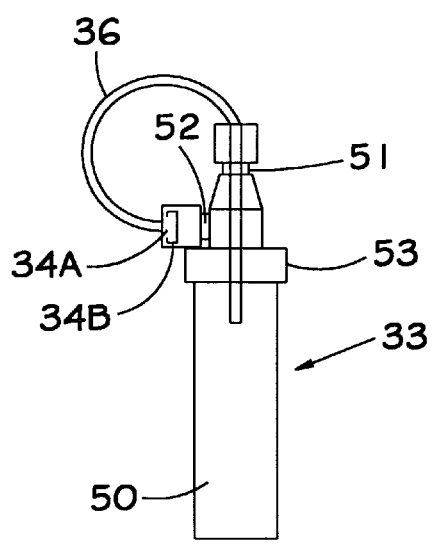
FIG. 4 is a diagram of a sample vial used in the closed positive pressure evaporation system of the invention.

Referring to FIG. 4, sample vial 33 comprises a container 50, air tight inlet cap 51 through which tubing 36 extends into container 50, air tight outlet cap 52 and collar 53. Tubing 36 terminates outside of sample vial 33 in half of a connector 34A. Outlet cap 52 includes the mating half of a connector 34B such that when connector 34A is joined to connector 34B, no air can flow into sample vial 33. Alternatively, a second length of tubing has one end connected to outlet cap 52 and the other end terminated in connector 34B which mates with connector 34A. Sample vial 33 is sealed, by connectors 34A and 34B, at the location from which the sample was obtained, thereby not exposing the sample to any outside contamination. Since the air in the sample vial is at the same air pressure as the air in the laboratory, there is minimal laboratory air introduced into the sample vial when the sample vial is being connected to the tubing in the chamber 25 thereby maintaining the integrity of the sample. The diameter of collar 53 is greater than the diameter of the holes in sample holders 41 such that sample vial 33 will be supported by the top sample holder 41.

Alternatively, connectors 34A and 34B may be located anywhere along the length of tubing 36.

Returning to FIG. 2, a collection manifold 35 has six inlet ports 54 and one outlet port 55. Each inlet port 54 is connected to tubing 37 which extends into chamber 25. Tubing 37 terminates in a connect 34A so as to mate with a connector 34B in outlet cap 52 of a sample vial 33. Outlet port 55 is connected to a scrubber 39 which is connected via tubing 57 to a waste flask 40. Waste Flask 40 should be located under an exhaust hood 18 for treatment of the exhaust fumes from the closed positive pressure evaporation system.

In operation, assuming that there are four sample vials, one blank vial and one control vial, the sample vials 33 are placed in positions 2, 3, 4 and 5 in the sample holder 41, the blank vial in position 1 in sample holder 41, and the control vial in position 6 in sample holder 41. Each vial is connected to the distribution and collection manifolds 23 and 35 as previously described. Open valve 21 and adjust the flow of purified inert gas, such as Nitrogen, to 6–8 psi (pounds per square inch) on the pressure gauge. Ensure that bubbles or circulation movement occurs in the scrubber which will indicate that there are no leaks in the system and will allow purified inert gas, such as Nitrogen, to replace the air in all the vials. Close the chamber and apply power to the heat source to obtain the desired temperature which in most cases will be full power. When the evaporation of the samples is complete, shut off power and allow the purified inert gas, such as Nitrogen, to flow for at least ten minutes to allow the samples and the vials to cool down and to purge any fumes and condensation droplets which have formed on the inside of the vials and tubing. When the vials are cool, shut off the purified inert gas, such as Nitrogen, and connect the vial tubing from the inlet of each vial to the outlet of each vial.

The temperature profile inside the chamber, at 60% power to the heat source, reaches a steady state condition in 60 minutes of 105 degrees centigrade. The temperature profile inside the chamber, at 100% power to the heat source, reaches a steady state condition in 30 minutes of 153 degrees centigrade at position 3 of the sample holder and of 148 degrees centigrade at position 6 of the sample holder.

Table I below shows the results of testing the closed positive pressure evaporation system to determine the evaporation rate (ml/hr) of samples as a function of position in the sample holder. The test used samples of de-ionized water, a purified inert gas, such as Nitrogen, flow of 5–6 psi, and power setting of 80% and 100%.

TABLE I

|       | Position |       |       |       |       |       |
|-------|----------|-------|-------|-------|-------|-------|
| Power | 1        | 2     | 3     | 4     | 5     | 6     |
| 80%   | 32.21    | 34.83 | 35.39 | 35.33 | 33.65 | 27.71 |
| 100%  | 40.65    | 42.56 | 42.90 | 43.21 | 42.41 | 38.12 |

Figure 1:
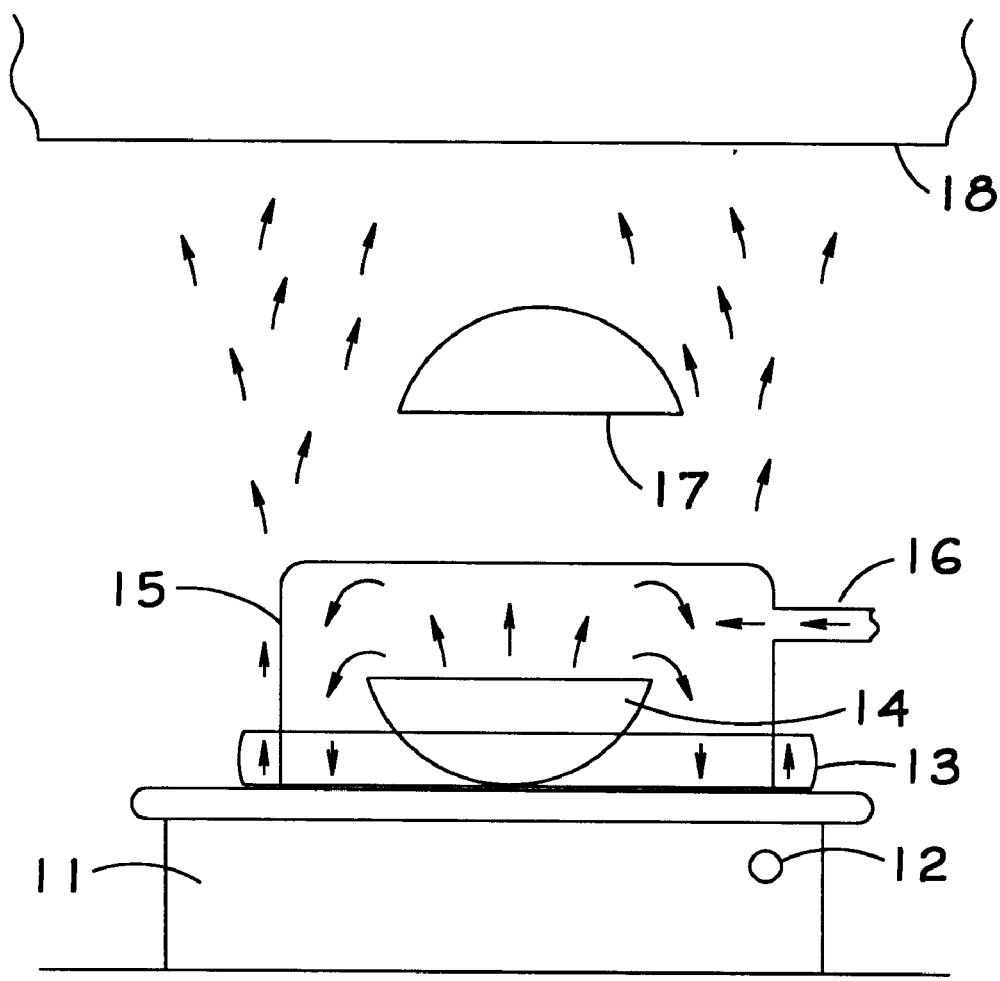
FIG. 1 is a diagram of a prior art open evaporation system.

The closed positive pressure evaporation system will evaporate a given sample approximately three times faster than the open evaporation system of FIG. 1 and the consumption of purified inert gas, such as Nitrogen, and electrical power will be reduced. More significant, the sensitivity of analytical procedures have been increased from 10 parts per million using the open evaporation system of FIG. 1, to as low as 1 part per billion using the closed positive pressure evaporation system of FIG. 2.

While the invention has been particularly shown and described with references to the preferred embodiments thereof, it will be understood by those skilled in the art that changes in form and detail may be made therein without departing from the spirit and scope of the invention. Given the above disclosure of general concepts and specific embodiments, the scope of the protection sought is defined by the following.

What is claimed is:

1. A closed positive pressure evaporation system for evaporating samples in a plurality of sample vials in preparation for analysis where each sample is in a separate sample vial of said plurality of sample vials, each said sample vial having an inlet means and an outlet means, said closed positive pressure evaporation system comprising:

a heat source:

a holder for positioning and holding said plurality of sample vials with reference to said heat source;

a chamber fully enclosing said a heat source and said holder for maintaining a constant temperature profile within said chamber when said samples within said plurality of sample vials being held by said holder are being heated by said heat source;

a distribution manifold connected via tubing to said inlet means of each sample vial of said plurality of sample vials, within said chamber being held in said holder, for distributing purified inert gas to each said sample vial;

a collection manifold connected via tubing to said outlet means of each of said sample vials, within said chamber and held in said holder, for collecting said purified inert gas and gases from each said sample vial connected to said distribution manifold;

each said sample vial of said plurality of sample vials comprising a sample vial connecting means for connecting said inlet means to said outlet means of said sample vial when said sample vial is not attached to said distribution manifold and said collection manifold for preventing contamination of said sample in said sample vial and for connecting said sample vial to said distribution manifold and said collection manifold.

2. The closed positive pressure evaporation system of claim 1 further comprising:

a scrubber, outside said chamber, attached via tubing to an outlet of said collection manifold for processing the purified inert gas and gases collected by said collection manifold when said evaporation system is evaporating at least one sample in said sample vial held in said holder.

3. The closed evaporator system of claim 1 further comprising a gas regulator for regulating the flow of said purified inert gas to said distribution manifold.

4. The closed evaporator system of claim 1 wherein said holder holds each said sample vial at an angle $\alpha$ from an upright position for providing a greater surface area of said sample in said sample vial to be exposed directly to heat generated by said heat source.

5. The closed positive pressure evaporation system of claim 4 wherein said angle $\alpha$ is within the range of 25 to 45 degrees.

6. The closed positive pressure evaporation system of claim 1 wherein said heat source is a variable heat source.

7. The closed positive pressure evaporation system of claim 1 further recovering components having a concentration as low as one part per billion from said samples being evaporated.

8. The closed positive pressure evaporation system of claim 1 having an evaporation rate of greater than 40 milliliters per hour for a sample of deionized water in said sample vial.

* * * * *